US012622912B2

(12) United States Patent
Li et al.

(10) Patent No.: US 12,622,912 B2
(45) Date of Patent: May 12, 2026

(54) APPLICATION OF PYRIDO[1,2-A]PYRIMIDINONE ANALOG

(71) Applicants: GUANGZHOU JOYO PHARMATECH CO., LTD, Guangdong (CN); SHANGHAI JIA TAN PHARMATECH CO., LTD., Shanghai (CN)

(72) Inventors: Yongguo Li, Shanghai (CN); Wei Wei, Shanghai (CN); Aiyun Song, Shanghai (CN); Wei Ye, Shanghai (CN)

(73) Assignees: GUANGZHOU JOYO PHARMATECH CO., LTD, Guangdong (CN); SHANGHAI JIA TAN PHARMATECH CO., LTD., Shanghai (CN)

( * ) Notice: Subject to any disclaimer, the term of this patent is extended or adjusted under 35 U.S.C. 154(b) by 408 days.

(21) Appl. No.: 18/260,472

(22) PCT Filed: Jan. 17, 2022

(86) PCT No.: PCT/CN2022/072322
§ 371 (c)(1),
(2) Date: Jul. 5, 2023

(87) PCT Pub. No.: WO2022/152296
PCT Pub. Date: Jul. 21, 2022

(65) Prior Publication Data

US 2024/0075038 A1 Mar. 7, 2024

(30) Foreign Application Priority Data

Jan. 18, 2021 (CN) ......................... 202110061761.8

(51) Int. Cl.
*A61P 35/00* (2006.01)
*A61K 31/519* (2006.01)

(52) U.S. Cl.
CPC ............ *A61K 31/519* (2013.01); *A61P 35/00* (2018.01)

(58) Field of Classification Search
CPC .............................. A61K 31/519; A61P 35/00
See application file for complete search history.

(56) References Cited

FOREIGN PATENT DOCUMENTS

| | | | | | |
|---|---|---|---|---|---|
| CN | 105461712 A | * | 4/2016 | ........... | C07D 471/04 |
| TW | 201602107 A | | 1/2016 | | |
| WO | WO-2015192761 A1 | * | 12/2015 | .............. | A61P 35/00 |
| WO | WO-2017101829 A1 | * | 6/2017 | ........... | C07D 471/04 |

OTHER PUBLICATIONS

Extended European Search Report issued by EPO on Jun. 10, 2024 for a corresponding EPO patent application No. 22739171.1.
First Examination Report issued by EPO on Jun. 21, 2024 for a corresponding EPO patent application No. 22739171.1.
First Examination Report issued by JPO on Jul. 2, 2024 for a corresponding a Japanese patent application No. 2023-543006.
Amer K Karam et al: “Cisplatin and P13kinase inhibition decrease invasion and migration of human ovarian carcinoma cells and regulate matrix-metalloproteinase expression”, Cytoskeleton, John Wiley & Sons, Inc, Hoboken, USA, vol. 67, No. 8, Jul. 6, 2010 (Jul. 6, 2010) , pp. 535-544.
F. Janku et al: P13K/AKT/mTOR Inhibitors in Patients With Breast and Gynecologic Malignancies Harboring PIK3CA Mutations, Journal of Clinical Oncology , vol. 30, No. 8, Jan. 23, 2012 (Jan. 23, 2012) , pp. 777-782.
Ali Alqahtani : “PIK3CA Gene Mutations in Solid Malignancies: Association with Clinicopathological Parameters and Prognosis”, Cancers , vol. 12, No. 1, Dec. 30, 2019 (Dec. 30, 2019) , p. 93.
Filip Janku et al: “Assessing PIK3CA and PTEN in Early—Phase Trials with P13K/AKT/mTOR Inhibitors”, Cell Reports, vol. 6, No. 2, Jan. 30, 2014 (Jan. 30, 2014) , pp. 377-387.
Second Examination Report issued by TWIPO on Nov. 22, 2024 for a corresponding a Taiwanese patent application No. 111101801.
Mar. 9, 2022 International Search Report issued in International Patent Application No. PCT/CN2022/072322.
Mar. 9, 2022 Written Opinion of the International Searching Authority issued in International Patent Application No. PCT/CN2022/072322.
Jul. 28, 2023 First Office Action issued in Taiwan( China) Patent Application No. 111101801.
Feb. 22, 2023 First Office Action issued in Chinese Patent Application No. 2022100022024.
Feb. 22, 2023 Search Report issued in Chinese Patent Application No. 2022100022024.
Sep. 9, 2023 Second Office Action issued in Chinese Patent Application No. 2022100022024.
Berge et al., “Pharmaceutical Salts”, Journal of Pharmaceutical Science 66: 1-19 (1977).
Handbook of Pharmaceutical Salts: Properties, Selection, and Use (P. Heinrich Stahl and Camille G. Wermuth, ed., Wiley-VCH, 2002.
Julia A. Beaver et al., “PIK3CA and AKT1 Mutations Have Distinct Effects on Sensitivity to Targeted Pathway Inhibitors in an Isogenic Luminal Breast Cancer Model System”, Clinical Cancer Research, 2013, 19(19): 5413~5422.

* cited by examiner

*Primary Examiner* — Erich A Leeser
(74) *Attorney, Agent, or Firm* — Houston Beshining Law Office PLLC; Liangang Ye

(57) ABSTRACT

An application of a pyrido[1,2-a]pyrimidinone analog or a pharmaceutically acceptable salt thereof in the preparation of a drug, the drug being used to treat and/or prevent one or more among PIK3CA-mutated breast cancer, PIK3CA-mutated ovarian cancer, PIK3CA-mutated endometrial cancer, PIK3CA-mutated cervical cancer, and PIK3CA-mutated bladder cancer.

15 Claims, 1 Drawing Sheet

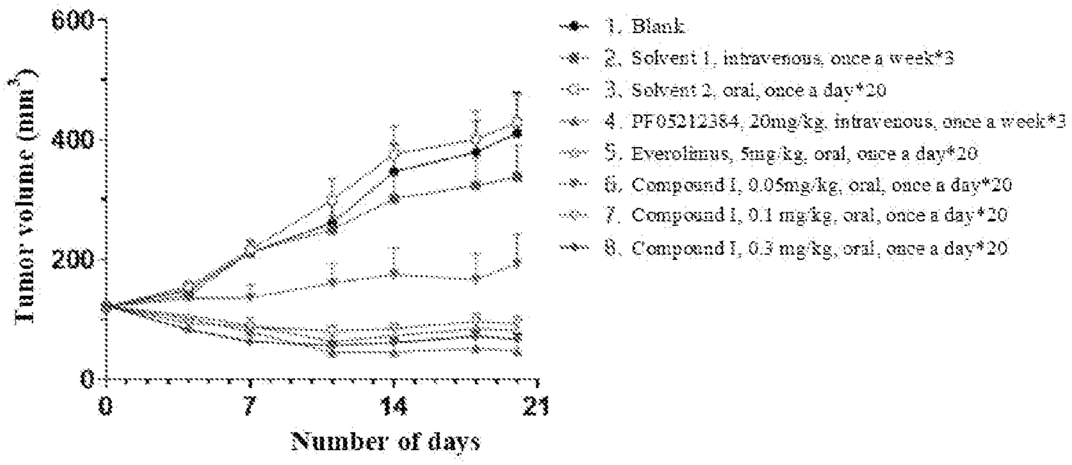
600
400
200
0
Tumor volume (mm$^3$)
0
7
14
21
Number of days
1. Blank
2. Solvent 1, intravenous, once a week*3
3. Solvent 2, oral, once a day*20
4. PF05212384, 20mg/kg, intravenous, once a week*3
5. Everolimus, 5mg/kg, oral, once a day*20
6. Compound I, 0.05mg/kg, oral, once a day*20
7. Compound I, 0.1 mg/kg, oral, once a day*20
8. Compound I, 0.3 mg/kg, oral, once a day*20

APPLICATION OF PYRIDO[1,2-A]PYRIMIDINONE ANALOG

The present application is a National Stage of International Application No. PCT/CN2022/072322, filed on Jan. 17, 2022, which claims priority of the Chinese Patent Application No. CN2021100617618 filed on Jan. 18, 2021, the content of which is incorporated herein by reference in its entirety.

TECHNICAL FIELD

The present disclosure relates to the technical field of biomedicine, in particular, the present disclosure relates to the application of pyrido[1,2-a]pyrimidinone analog.

BACKGROUND

Malignant tumors are a type of disease that seriously threatens human life and health at present, whose morbidity and mortality are increasing year by year. Human mortality due to cancer ranks second only to cardiovascular and cerebrovascular diseases. The essence of carcinogenesis is that the molecular signals that regulate the physiological functions of cells are abnormal in the transduction process, which leads to the disorder of normal physiological functions of cells and infinite proliferation. Cell signal transduction is closely related to tumor occurrence, development, recurrence and metastasis. Traditional cytotoxic drugs for tumor treatment generally have disadvantages such as low selectivity, strong side effects and poor drug resistance, which promotes the transfer of the research direction of anti-tumor drugs to small molecule targeting drugs.

PI3K-AKT-mTOR is an important pathway of cell cycle regulation, which is crucial to cell growth, division, survival and reproduction. Its transitional activation is involved in the occurrence, development, survival and migration of various tumors. PI3K (phosphatidylinositol 3-kinase), AKT and mTOR (mammalian target of rapamycin) are the key molecules of this pathway, so they become the targets of anti-tumor therapy. PI3K-specific or mTOR-specific inhibitors are already on the market, and the dual inhibitors of these two molecules can theoretically have better anti-tumor efficacy.

PF-05212384 (PKI-587) is a PI3K and mTOR dual-target inhibitor developed by Pfizer, which is currently in Phase II clinical trials. Everolimus is an oral mTOR single-target inhibitor developed by Novartis, with a trade name of Afinitor, which was approved for marketing by the FDA in March 2009. Internationally, Everolimus is approved for multiple indications: advanced renal cell carcinoma (RCC), tuberous sclerosis-associated subependymal giant cell astrocytoma (TSC-SEGA) and renal angiomyolipoma (TSC-AML), advanced pancreatic neuroendocrine tumors (pNET), postmenopausal estrogen receptor positive/HER-2 negative advanced breast cancer (BC) and other tumors.

CONTENT OF THE PRESENT INVENTION

The purpose of the present disclosure is to provide an application of pyrido[1,2-a]pyrimidinone analog. Such compound or a pharmaceutically acceptable salt thereof has good antitumor activity against PIK3CA-mutated cancers, such as one or more of PIK3CA-mutated breast cancer, PIK3CA-mutated ovarian cancer, PIK3CA-mutated endometrial cancer, PIK3CA-mutated cervical cancer, and PIK3CA-mutated bladder cancer.

The present disclosure provides a use of compound I or a pharmaceutically acceptable salt thereof in the preparation of a medicament, the structure of the compound I is as follows:

I

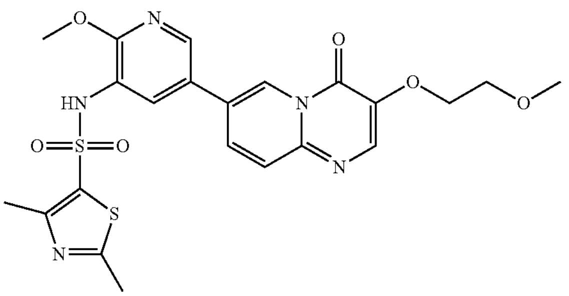

the medicament is used for treating and/or preventing PIK3CA-mutated cancer.

Wherein, the PIK3CA-mutated cancer can be PIK3CA-mutated breast cancer.

The PIK3CA-mutated cancer can be PIK3CA-mutated ovarian cancer.

The PIK3CA-mutated cancer can be PIK3CA-mutated endometrial cancer.

The PIK3CA-mutated cancer can be PIK3CA-mutated cervical cancer.

The PIK3CA-mutated cancer can be PIK3CA-mutated bladder cancer.

In the present disclosure, the medicament is presented in an oral dosage form.

In the present disclosure, the medicament is presented in a tablet form.

The PIK3CA-mutated ovarian cancer can be PIK3CA-mutated ovarian clear cell carcinoma, for example, PIK3CA-mutated left ovarian clear cell carcinoma.

The PIK3CA-mutated ovarian cancer can be PIK3CA-mutated ovarian cancer with metastasis, and the metastasis can be liver metastasis.

The PIK3CA-mutated ovarian cancer can be ovarian cancer that is ineffective to the first-line or second-line treatment.

The PIK3CA-mutated cervical cancer can be PIK3CA-mutated cervical squamous cell carcinoma.

The PIK3CA-mutated cervical cancer can be PIK3CA-mutated cervical cancer with metastasis, and the metastasis can be lymph and/or lung. The lymph can be left supraclavicular lymph and/or retroperitoneal lymph.

The PIK3CA-mutated cervical cancer can be cervical cancer that is ineffective to the first-line, second-line treatment or the third-line treatment.

The present disclosure further provides the compound I or the pharmaceutically acceptable salt thereof for use in treating and/or preventing PIK3CA-mutated cancer, the structure of the compound I is as follows:

I

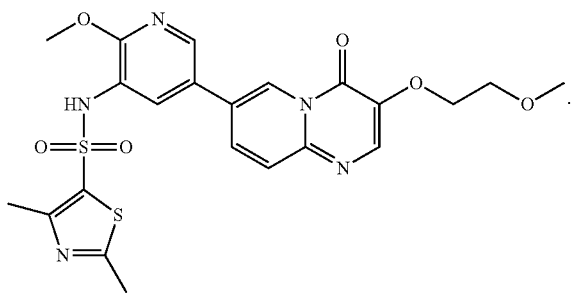

Herein, the PIK3CA-mutated cancer is as described in any of the above embodiments.

The present disclosure provides a method for treating and/or preventing PIK3CA-mutated cancer, comprising administering to a patient a therapeutically effective amount of the compound I or the pharmaceutically acceptable salt thereof. The PIK3CA-mutated cancer is as described in any of the above embodiments.

In the use of the compound I or the pharmaceutically acceptable salt thereof in the preparation of a medicament or the method for treating and/or preventing PIK3CA-mutated cancer, the dosage of the compound I or the pharmaceutically acceptable salt thereof can be administered according to the weight of the subject/patient. Preferably, the administration dosage of the compound I or the pharmaceutically acceptable salt thereof is 0.1-2.0 mg/time, for example: 0.1 mg/time, 0.2 mg/time, 0.3 mg/time, 0.4 mg/time, 0.5 mg/time, 0.6 mg/time, 0.7 mg/time, 0.8 mg/time, 0.9 mg/time, 1.0 mg/time, 1.1 mg/time, 1.2 mg/time, 1.3 mg/time, 1.4 mg/time, 1.5 mg/time, 1.6 mg/time, 1.7 mg/time, 1.8 mg/time, 1.9 mg/time or 2.0 mg/time.

In the use or the method for treating and/or preventing PIK3CA-mutated cancer, the administration frequency of the compound I or the pharmaceutically acceptable salt thereof can be once a day or twice a day.

In the use or the method for treating and/or preventing PIK3CA-mutated cancer, the compound I or the pharmaceutically acceptable salt thereof can be administered orally.

Preferably, in the use or the method for treating and/or preventing cancer, the compound I or the pharmaceutically acceptable salt thereof is administered orally, and the administration dosage is 0.1-2.0 mg/time, for example, 0.1 mg/time, 0.4 mg/time, 0.5 mg/time, 0.6 mg/time, 0.7 mg/time, 0.9 mg/time or 1.1 mg/time, and the administration frequency is once a day or twice a day.

In the use or the method for treating and/or preventing PIK3 CA-mutated cancer, it can further include the step of detecting whether the patient carries PIK3CA gene mutation.

The present disclosure also provides a combined kit, comprising kit A and kit B;

wherein the kit A comprises reagents for detecting PIK3CA gene mutation; the kit B comprises the compound I or the pharmaceutically acceptable salt thereof.

Preferably, the administration time of the kit A and the kit B is in no particular order, or the kit A is administered first between the kits.

Preferably, in the kit A, the reagent for detecting PIK3CA gene mutation is used for detecting whether a cancer patient carries PIK3CA gene mutation; for example, the cancer patient is the patient with one or more than one of breast cancer, ovarian cancer, endometrial cancer, cervical cancer and bladder cancer.

Preferably, in the kit B, the amount of the compound I or the pharmaceutically acceptable salt thereof is a therapeutically effective amount.

Preferably, the kit B also comprises pharmaceutically acceptable excipients.

Preferably, in the kit B, the dosage and administration frequency of the compound I or the pharmaceutically acceptable salt thereof are as described in any of the above embodiments.

Preferably, the combined kit is used for treating and/or preventing PIK3CA-mutated cancer, and the PIK3 CA-mutated cancer is as described in any of the above embodiments.

Unless otherwise specified, the following terms and phrases used herein are intended to have the following meanings. A specific term or phrase should not be considered indefinite or unclear if it is not specifically defined, but should be understood according to its ordinary meaning. When a trade name appears herein, it is intended to refer to its corresponding trade name or its active ingredient.

The term "pharmaceutically acceptable" as used herein refers to those compounds, materials, compositions and/or dosage forms, which are suitable for use in contact with human and animal tissues within the scope of sound medical judgment, without undue toxicity, irritation, allergic reaction or other problems or complications, commensurate with a reasonable benefit/risk ratio.

The term "pharmaceutically acceptable salt" refers to a salt prepared from the compound of the present disclosure with a relatively non-toxic, pharmaceutically acceptable acid or base. When the compound of the present disclosure contains relatively acidic functional groups, the base addition salt can be obtained by contacting the neutral form of such compound with a sufficient amount of a pharmaceutically acceptable base in pure solution or in a suitable inert solvent. Pharmaceutically acceptable base addition salts include but are not limited to lithium salts, sodium salts, potassium salts, calcium salts, aluminum salts, magnesium salts, zinc salts, bismuth salts, ammonium salts, diethanolamine salts. When the compound of the present disclosure contains relatively basic functional groups, the acid addition salt can be obtained by contacting the neutral form of such compound with a sufficient amount of a pharmaceutically acceptable acid in pure solution or in a suitable inert solvent. The pharmaceutically acceptable acid includes inorganic acids. The inorganic acids include but not limited to hydrochloric acid, hydrobromic acid, hydroiodic acid, nitric acid, carbonic acid, phosphoric acid, phosphorous acid, sulfuric acid and the like. The pharmaceutically acceptable acids include organic acids. The organic acids include but not limited to acetic acid, propionic acid, oxalic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, salicylic acid, tartaric acid, methanesulfonic acid, isonicotinic acid, acid citric acid, oleic acid, tannic acid, pantothenic acid, bitartaric acid, ascorbic acid, gentisic acid, fumaric acid, gluconic acid, sugar acid, formic acid, ethanesulfonic acid, pamoic acid (i.e., 4,4'-methylene-bis(3-hydroxy-2-naphthoic acid), amino acids (such as glutamic acid, arginine), etc. When the compound of the present disclosure contains relatively acidic and relatively basic functional groups, it can be converted into base addition salts or acid addition salts. For details, see Berge et al., "Pharmaceutical Salts", Journal of Pharmaceutical Science 66: 1-19 (1977), or, Handbook of Pharmaceutical Salts: Properties, Selection, and Use (P. Heinrich Stahl and Camille G. Wermuth, ed., Wiley-VCH, 2002).

The term "treatment" refers to therapeutic therapy. In relation to a specific condition, treatment means: (1) one or more biological manifestations of amelioration of the disease or condition, (2) interference with (a) one or more points in the biological cascade leading to or causing the condition or (b) one or more biological manifestations of the condition, (3) amelioration of one or more symptoms, effects or side effects associated with the condition, or one or more symptoms, effects or side effects associated with the condition or the treatment thereof, or (4) amelioration of the condition or the development of one or more biological manifestations of the condition.

The term "prevent" refers to a reduction in the risk of contracting or developing a disease or disorder.

The term "therapeutically effective amount" refers to an amount of a compound sufficient to effectively treat a disease or condition described herein when administered to a patient. A "therapeutically effective amount" will vary depending on the compound, the condition and the severity thereof, and the age of the patient to be treated, but can be adjusted as necessary by those skilled in the art.

The term "pharmaceutically acceptable excipients" refers to the excipients and additives used in the production of medicaments and formulation of prescriptions, and refers to all substances contained in the pharmaceutical formulation except active ingredients. See Pharmacopoeia of the People's Republic of China (2020 Edition) Volume Four or Handbook of Pharmaceutical Excipients (Raymond C Rowe, 2009 Sixth Edition).

The term "patient" refers to any animal, preferably a mammal, and most preferably a human, that is about to or has received the administration of the compound according to the examples of the present disclosure. The term "mammal" includes any mammal. Examples of mammals include but are not limited to cows, horses, sheep, pigs, cats, dogs, mice, rats, rabbits, guinea pigs, monkeys, humans, etc., most preferably a human.

On the basis of not violating common knowledge in the art, the above-mentioned preferred conditions can be combined arbitrarily to obtain preferred examples of the present disclosure.

The reagents and raw materials used in the present disclosure are all commercially available.

The positive and progressive effect of the present disclosure is that compound I has good antitumor activity against one or more than one of PIK3CA-mutated breast cancer, PIK3CA-mutated ovarian cancer, PIK3CA-mutated cervical cancer, PIK3CA-mutated endometrial cancer, and PIK3CA-mutated bladder cancer.

BRIEF DESCRIPTION OF THE DRAWINGS

FIG. 1 is the in vivo drug efficacy result of compound I on human breast cancer BT-474 xenograft tumor.

DETAILED DESCRIPTION OF THE PREFERRED EMBODIMENT

The present disclosure is further illustrated below by means of examples, but the present disclosure is not limited to the scope of the examples. The experimental methods without illustrated specific conditions in the following examples are selected according to conventional methods and conditions, or according to the product instructions.

Compound I in the following examples refers to

I

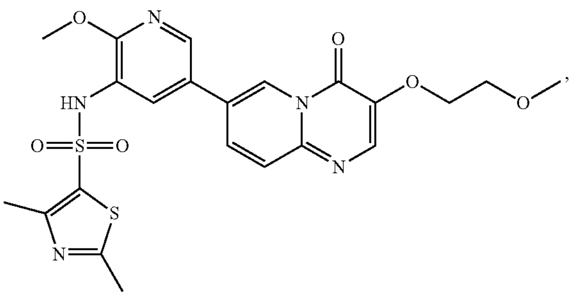

which is a pyrido[1,2-a]pyrimidinone analog.

Example 1 the $IC_{50}$ of the Inhibitory Effect of the Tested Compound Ion the Kinase Activity of PIK3CA Mutants In Vitro

1. Experimental Materials and Methods

Main reagents: human PI3K p110α/p85α (purchased from Promega, Cat. No. V1721), human PI3K p110α (E542K)/p85α (purchased from Millipore, Cat. No. 14-782), human PI3K p110α (E545K)/p85α (purchased from Millipore, Cat. No. 14-783) and human PI3K p110α (H1047R)/p85α (purchased from Millipore, Cat. No. 14-792)

Experimental Methods

1) Compound was prepared. The initial concentration of compound I was 100 nM, and was serially diluted 3-fold to 10 concentrations and transferred to the test plate.

2) Human PI3K p110α/p85α, human PI3K p110α (E542K)/p85α, human PI3K p110α (E545K)/p85α or human PI3K p110α (H1047R)/p85α and assay buffer (10 μM phosphatidylinositol 4,5-bisphosphate and Mg/ATP) were incubated. The reaction was initiated by adding ATP solution and incubated for 30 min.

3) After incubation for 30 minutes, the reaction was terminated by adding stop solution. The stop solution contained EDTA, biotinylated phosphatidylinositol-3,4,5-trisphosphate.

4) Detection buffer was added, europium-tagged anti-GST monoclonal antibody, GST-tagged GRP1 PH domain, and streptavidin allophycocyanin.

5) The plate was read and the HTRF value was calculated according to the formula HTRF=10000×(Em665 nm/Em620 nm). GraphPad Prism 5.0 software was used, and a S-type dosage-survival rate curve was drawn using a nonlinear regression model and $IC_{50}$ value was calculated.

2. Experimental Results

TABLE 1

| IC50 values of compound I on detected PI3Kα kinases and the mutants thereof | |
|---|---|
| Kinase name | Compound I $IC_{50}$ (nM) |
| PI3K p110α/p85α | 1 |
| PI3K p110α (E542K)/p85α | 3 |
| PI3K p110α (H1047R)/p85α | 2 |
| PI3K p110α (E545K)/p85α | 1 |

It could be seen from the experimental results in Table 1 that compound I not only had a strong inhibitory effect on PI3Kα kinase ($IC_{50}$=1 nM), but also had the similar inhibitory effect on three typical mutants (E542K, H1047R and E545K) as wild type.

Example 2 the $IC_{50}$ of Compound I on PIK3CA-Mutated Breast Cancer Cell Lines was Determined by CTG Method 1. Experimental Materials and Methods (1) Cell Lines

TABLE 2

| PIK3CA-mutated breast cancer cell lines | | | | |
|---|---|---|---|---|
| Cell name | Organization type | Cultural charac-teristics | Culture medium | Cells seeded per well |
| BT-474 | Breast | Adherent | MEM + 10% FBS(or DMEM + 10% FBS + 10 μg/mL Insulin) | 6000 |
| T47D | Breast | Adherent | RPMI1640 + 10% FBS + 0.2 U/mL Insulin | 5500 |

Note:
a. Cell culture conditions were: 37° C., 5% $CO_2$ and 95% humidity;
b. $IC_{50}$ value: the concentration of inhibitor when 50% inhibitory effect was achieved;
c. BT-474 and T47D were PIK3CA-mutated breast cancer cell lines. PIK3CA-mutated BT-474 and T47D cells were purchased from ATCC, wherein ATCC ® No. was HTB-20 ™ and HTB-133 ™, respectively.
d. The percentage in 10% FBS in Table 2 was volume percentage.

(2) Reagents
1) FBS (fetal bovine serum) (purchased from ExCell, product number: FND500);
2) DMEM medium (purchased from Gibco, product number: C11995500BT);
3) Insulin (purchased from Gibco, product number: EPX010-12003-901);
4) RPMI1640 medium (purchased from Hyclone, product number: SH30809.01);
5) MEM medium (purchased from Hyclone, product number: SH30024.01).

(3) Test Article and Positive Control Article

Test article: compound I;

Positive control article: Cisplatin, Molecular weight: 300.05; Solvent: PBS (phosphate buffer saline); Storage condition: 2-8° C.; Supplier: Qilu Pharmaceutical.

(4) The CTG Method was Used to Determine the Cell Proliferation $IC_{50}$ of the Compound.

Step 1: Cells in exponential growth phase were harvested, and viable cells were counted with a Vi-Cell XR cytometer. The cell suspension was adjusted to an appropriate concentration with medium. 90 μL of cell suspension was added to each well of a 96-well cell culture plate, and the final cell concentration was 1500-6000 cells/well.

Step 2: The initial concentration of administration of compound I was 3 μM, and the initial concentration of administration of the control drug Cisplatin was 100 μM, and serially diluted 3-fold, a total of 9 concentration gradients and a DMSO control, the final concentration of DMSO in each well was 0.1%, placed in a 37° C., 5% $CO_2$ incubator for 72 hours.

Step 3: After 72 hours of drug treatment, 50 μL (½ culture volume) CTG solution that was melted and equilibrated to room temperature was added to each well according to the CTG operation instruction. The solution was mixed well with a microplate shaker for 2 minutes, and placed at room temperature. After 10 minutes, the fluorescence signal value was measured with an Envision2104 plate reader.

(5) Data Analysis

Cell survival rate was calculated using the formula: $V_{sample}/V_{vehicle\ control}\times 100\%$. Where, $V_{sample}$ was the reading of the drug treatment group, and $V_{vehicle\ control}$ was the average value of the solvent control group. GraphPad Prism 5.0 software was used, and a S-type dosage-survival rate curve was drawn using a nonlinear regression model and $IC_{50}$ value was calculated.

2. Experimental Results

TABLE 3

| $IC_{50}$ values of compound I and Cisplatin on each tested cell line | | |
|---|---|---|
| Cell name | Compound I Absolute $IC_{50}$ (μM) | Cisplatin Absolute $IC_{50}$ (μM) |
| T47D | 0.017 | 36.636 |
| BT-474 | 0.021 | >100 |

It could be seen from the experimental results in Table 3 that the concentration of the inhibitor was lower than 1 μM when compound I achieved 50% inhibitory effect on T47D and BT-474 tumor cells.

Example 3 the $IC_{50}$ of Compound I on PIK3CA-Mutated Cervical Cancer Cell Lines was Determined by CTG Method 1. Experimental Materials and Methods (1) Cell Lines

TABLE 4

| Cervical cancer cell lines with PIK3CA mutation | | | | |
|---|---|---|---|---|
| Cell name | Organi-zation type | Cultural charac-teristics | Culture medium | Cells seeded per well |
| ME-180 | Cervix | Adherent | McCoy's 5A + 10% FBS | 2500 |
| Ca Ski | Cervix | Adherent | RPMI-1640 + 10% FBS | 2500 |
| C-33 A | Cervix | Adherent | MEM + 10% FBS + 1% MEM NEAA + 1% sodium pyruvate | 2000 |

Note:
a. Cell culture conditions were: 37° C., 5% $CO_2$ and 95% humidity.
b. ME-180 and Ca Ski and C-33 were PIK3CA-mutated cervical cancer cell lines. PIK3CA-mutated ME-180, Ca Ski and C-33 A cells were purchased from ATCC, wherein ATCC ® No. was HTB-33 ™, CRL-1550 ™ and HTB-31 ™, respectively.
c. The percentages in 10% FBS, 1% MEM NEAA and 1% sodium pyruvate in Table 4 were volume percentages.

(2) Reagents

1) FBS (fetal bovine serum) (purchased from ExCell, product number: FND500);
2) RPMI1640 medium (purchased from Hyclone, product number: SH30809.01);
3) McCoy's 5A medium (purchased from Gibco, product number: 12330-031);
4) MEM medium (purchased from Hyclone, product number: SH30024.01;
5) MEM NEAA (purchased from Gibco, product number: 11140-050);
6) Sodium pyruvate (purchased from Gibco).

(3) Test Article and Positive Control Article

Test article: compound I;

Positive Control Article:

1) Alpelisib, molecular weight: 441.47; solvent: DMSO; storage condition after dissolution: −20° C.; supplier: Shanghai TOPSCIENCE Biochemical Technology Co., Ltd., CAS number: 1217486-61-7;
2) Cisplatin, molecular weight: 300.05; solvent: PBS (phosphate buffer saline); storage condition: 2-8° C.; supplier: Qilu Pharmaceutical.

(4) The CTG Method was Used to Determine the Cell Proliferation $IC_{50}$ of the Compound Step 1: Cells in exponential growth phase were harvested, and viable cells were counted with a Vi-Cell XR cytometer. The cell suspension was adjusted to an appropriate concentration with medium. 90 μL of cell suspension was added to each well of a 96-well cell culture plate, and the final cell concentration was 1500-6000 cells/well.

Step 2: The initial concentration of administration of compound I and the control drug Alpeli sib was 3 μM, and the initial concentration of administration of the control drug Cisplatin was 100 μM, serially diluted 3-fold, a total of 9 concentration gradients and a DMSO control, the final concentration of DMSO in each well was 0.1%, placed in a 37° C., 5% $CO_2$ incubator for 72 hours.

Step 3: After 72 hours of drug treatment, 50 μL (½ culture volume) CTG solution that was melted and equilibrated to room temperature was added to each well according to the CTG operation instruction. The solution was mixed well with a microplate shaker for 2 minutes, and placed at room temperature. After 10 minutes, the fluorescence signal value was measured with an Envision2104 plate reader.

(5) Data Analysis

Cell survival rate was calculated using the formula: $V_{sample}/V_{vehicle\ control}\times100\%$. Where, $V_{sample}$ was the reading of the drug treatment group, and $V_{vehicle\ control}$ was the average value of the solvent control group. GraphPad Prism 5.0 software was used, and a S-type dosage-survival rate curve was drawn using a nonlinear regression model and $IC_{50}$ value was calculated.

2. Experimental Results

TABLE 5

$IC_{50}$ values of compound I, Alpelisib and Cisplatin on each tested cell line

| Cell name | Compound I Absolute $IC_{50}$ (μM) | Alpelisib Absolute $IC_{50}$ (μM) | Cisplatin Absolute $IC_{50}$ (μM) |
|---|---|---|---|
| ME-180 | 0.015 | 2.066 | 2.833 |
| Ca Ski | 0.039 | >3 | 16.182 |
| C-33A | 0.180 | >3 | 3.563 |

Conclusion: Compound I significantly inhibited the growth of PIK3CA-mutated cervical cancer cells, and the half inhibitory concentration was between 0.015-0.180 μM, while the control compound Alpelisib was basically ineffective, and the half inhibitory concentration thereof was higher than the maximum concentration of 3 μM in the two cell lines; in addition, compound I inhibited the growth of PIK3CA-mutated cervical cancer cells better than the control compound Cisplatin.

Example 4 the $IC_{50}$ of Compound I on PIK3CA-Mutated Bladder Cancer Cell Lines was Determined by CTG Method 1. Experimental Materials and Methods (1) Cell Lines

TABLE 6

PIK3CA-mutated bladder cancer cell lines

| Cell name | Organization type | Cultural characteristics | Culture medium | Cells seeded per well |
|---|---|---|---|---|
| J82 | Bladder | Adherent | MEM + 10% FBS | 1000 |
| TCCSUP | Bladder | Adherent | MEM + 10% FBS + 1% MEM NEAA + 1% sodium pyruvate | 2500 |

Note:
a. Cell culture conditions were: 37° C., 5% $CO_2$ and 95% humidity.
b. J82 and TCCSUP were PIK3CA-mutated bladder cancer cell lines. PIK3CA-mutated J82 and TCCSUP cells were purchased from ATCC, wherein ATCC ® No. was HTB-1 ™ and HTB-5 ™, respectively.
c. The percentages in 10% FBS, 1% MEM NEAA and 1% sodium pyruvate in Table 6 were volume percentages.

(2) Reagents

1) FBS (fetal bovine serum) (purchased from ExCell, product number: FND500);
2) MEM medium (purchased from Hyclone, product number: SH30024.01;
3) MEM NEAA (purchased from Gibco, product number: 11140-050);
4) Sodium pyruvate (purchased from Gibco).

(3) Test Article and Positive Control Article

Test article: compound I;

Positive Control Article:

1) Erdafitinib, molecular weight: 446.55; solvent: DMSO; storage condition after dissolution: −8° C.; supplier: Shanghai TOPSCIENCE Biochemical Technology Co., Ltd., CAS number: 1346242-81-6;
2) Cisplatin, molecular weight: 300.05; solvent: PBS (phosphate buffer saline); storage condition: 2-8° C.; supplier: Qilu Pharmaceutical.

(4) The CTG Method was Used to Determine the Cell Proliferation $IC_{50}$ of the Compound Step 1: Cells in exponential growth phase were harvested, and viable cells were counted with a Vi-Cell XR cytometer. The cell suspension was adjusted to an appropriate concentration with medium. 90 μL of cell suspension was added to each well of a 96-well cell culture plate, and the final cell concentration was 1500-6000 cells/well.

Step 2: The initial concentration of administration of compound I and the control drug Erdafitinib was 3 μM, and the initial concentration of administration of the control drug Cisplatin was 100 μM, serially diluted 3-fold, a total of 9 concentration gradients and a DMSO control, the final concentration of DMSO in each well was 0.1%, placed in a 37° C., 5% $CO_2$ incubator for 72 hours.

Step 3: After 72 hours of drug treatment, 50 μL (½ culture volume) CTG solution that was melted and equilibrated to room temperature was added to each well according to the CTG operation instruction. The solution was mixed well with a microplate shaker for 2 minutes, and placed at room temperature. After 10 minutes, the fluorescence signal value was measured with an Envision2104 plate reader.

(5) Data Analysis

Cell survival rate was calculated using the formula: $V_{sample}/V_{vehicle\ control}\times100\%$. Where, $V_{sample}$ was the reading of the drug treatment group, and $V_{vehicle\ control}$ was the average value of the solvent control group. GraphPad Prism 5.0 software was used, and a S-type dosage-survival rate curve was drawn using a nonlinear regression model and $IC_{50}$ value was calculated.

2. Experimental Results

TABLE 7

$IC_{50}$ values of compound I, Erdafitinib and Cisplatin on each tested cell line

| Cell name | Compound I Absolute $IC_{50}$ (μM) | Erdafitinib Absolute $IC_{50}$ (μM) | Cisplatin Absolute $IC_{50}$ (μM) |
|---|---|---|---|
| J82 | 0.278 | >3 | 1.727 |
| TCCSUP | 0.223 | >3 | 3.768 |

Conclusion: Compound I significantly inhibited the growth of PIK3CA-mutated bladder cancer cells, and the half inhibitory concentration was within 1 μM, while the control compound Erdafitinib was basically ineffective, and the half inhibitory concentration thereof in the two cell lines was higher than the maximum concentration of 3 μM; in addition, compound I inhibited the growth of PIK3CA-mutated bladder cancer cells better than the control compound Cisplatin.

Example 5 the $IC_{50}$ of Compound I on PIK3CA-Mutated Endometrial Cancer Cell Lines was Determined by CTG Method 1. Experimental Materials and Methods (1) Cell Lines

TABLE 8

PIK3CA-mutated endometrial cancer cell lines

| Cell name | Organization type | Cultural charac-teristics | Culture medium | Cells seeded per well |
|---|---|---|---|---|
| HEC-1-A | Endometrium | Adherent | McCoy's 5A + 10% FBS | 3000 |
| HEC-1-B | Endometrium | Adherent | MEM + 10% FBS | 3000 |

Note:

a. Cell culture conditions were: 37° C., 5% $CO_2$ and 95% humidity.

b. HEC-1-A and HEC-1-B were PIK3CA-mutated endometrial cancer cell lines, PIK3CA-mutated HEC-1-A and HEC-1-B cells were purchased from ATCC, wherein ATCC ® No. was HTB -112 ™ and HTB-113 ™.

c. The percentage in 10% FBS in Table 8 was volume percentage.

(2) Reagents

1) FBS (fetal bovine serum) (purchased from ExCell, product number: FND500);

2) McCoy's 5A medium (purchased from Gibco, product number: 12330-031);

3) MEM medium (purchased from Hyclone, product number: SH30024.01).

(3) Test Article and Positive Control Article

Test article: compound I;

Positive control article: Alpelisib, molecular weight: 441.47; solvent: DMSO; storage condition after dissolution: −20° C.; supplier: Shanghai TOPSCIENCE Biochemical Technology Co., Ltd., CAS number: 1217486-61-7;

(4) The CTG Method was Used to Determine the Cell Proliferation $IC_{50}$ of the Compound Step 1: Cells in exponential growth phase were harvested, and viable cells were counted with a Vi-Cell XR cytometer. The cell suspension was adjusted to an appropriate concentration with medium. 90 μL of cell suspension was added to each well of a 96-well cell culture plate, and the final cell concentration was 1500-6000 cells/well.

Step 2: The initial concentration of administration of compound I and the control drug Alpelisib was 3 μM, serially diluted 3-fold, a total of 9 concentration gradients and a DMSO control, the final concentration of DMSO in each well was 0.1%, placed in a 37° C., 5% $CO_2$ incubator for 72 hours.

Step 3: After 72 hours of drug treatment, 50 μL (½ culture volume) CTG solution that was melted and equilibrated to room temperature was added to each well according to the CTG operation instruction. The solution was mixed well with a microplate shaker for 2 minutes, and placed at room temperature. After 10 minutes, the fluorescence signal value was measured with an Envision2104 plate reader.

(5) Data Analysis

Cell survival rate was calculated using the formula: $V_{sample}/V_{vehicle\ control}\times100\%$. Where, $V_{sample}$ was the reading of the drug treatment group, and $V_{vehicle\ control}$ was the average value of the solvent control group. GraphPad Prism 5.0 software was used, and a S-type dosage-survival rate curve was drawn using a nonlinear regression model and $IC_{50}$ value was calculated.

2. Experimental Results

TABLE 9

$IC_{50}$ values of compound I and Alpelisib on each tested cell line

| Cell name | Compound I Absolute $IC_{50}$ (μM) | Alpelisib Absolute $IC_{50}$ (μM) |
|---|---|---|
| HEC-1-A | 0.048 | 2.464 |
| HEC-1-B | 0.052 | 2.414 |

Conclusion: Compound I significantly inhibited the growth of PIK3CA-mutated endometrial cancer cells, and the half inhibitory concentration was within 0.1 μM, while the control compound Alpelisib was higher than 2 uM. Compared with the control drug, compound I had a significant curative effect on PIK3CA-mutated endometrial cancer.

Example 6 Study on the In Vivo Pharmacodynamics of the Test Drug on Human Breast Cancer BT-474 Subcutaneous Xenograft Tumor BALB/C Nude Mouse Model Experimental purpose: Study the in vivo efficacy of the test drug on human breast cancer BT-474 subcutaneous xenograft tumor BALB/c nude mouse model.

Experimental Design (1) Cell culture: human breast cancer BT-474 cells were monolayer cultured in vitro. The culture conditions were that 10% fetal bovine serum, 100 U/ml penicillin (purchased from Gibco) and 100 μg/ml chain Mycin (purchased from Gibco) were added to Hybri-Care medium, and cultured at 37° C. and 5% $CO_2$. Routine digestion and passage were performed with trypsin-EDTA (purchased from Gibco, product number: 25200-072) twice a week. When the cell saturation was 80%-90%, the cells are harvested, counted and inoculated.

(2) Animals: BALB/c nude mice, female, 6 weeks old, weighing 16-18 grams. Provided by Shanghai Sippe-Bk Lab Animal Co., Ltd.

(3) Control article:

Both PF05212384 and Everolimus were purchased from Shanghai TOPSCIENCE Biochemical Technology Co., Ltd.

(4) Tumor inoculation: 0.2 ml ($1\times10^7$) BT-474 cells (matrigel was added, volume 1:1) were subcutaneously inoculated on the right back of each mouse, and the mice were divided into groups and administered with drugs when the average tumor volume reached 122 $mm^3$. See Table 10 below for the experimental grouping and dosing regimen.

TABLE 10

Experimental grouping and dosing regimen of the tested drug on the human breast cancer BT-474 cell model

| Group | Number of animals | Drug | Dose (mg/kg) | Administration volume (μL/g) | Route of administration | Administration frequency |
|---|---|---|---|---|---|---|
| 1 | 9 | Blank control group | — | 10 | — | — |
| 2 | 9 | Solvent 1 | — | 10 | Vein | Once a week for 3 weeks |
| 3 | 9 | Solvent 2 | — | 10 | Oral | Once a day for 20 days |
| 4 | 9 | PF05212384 | 20 | 10 | Vein | Once a week for 3 weeks |
| 5 | 9 | Everolimus | 5 | 10 | Oral | Once a day for 20 days |
| 6 | 9 | Compound I | 0.05 | 10 | Oral | Once a day for 20 days |
| 7 | 9 | Compound I | 0.1 | 10 | Oral | Once a day for 20 days |
| 8 | 9 | Compound I | 0.3 | 10 | Oral | Once a day for 20 days |

Note:
Solvent 1: Mixture of propylene glycol, Tween-80 and 5% glucose solution (v:v:v = 30:5:65).
Solvent 2: 1% methylcellulose, the percentage was volume percentage.

(4) In vivo efficacy results: as shown in FIG. 1 and Table 11.

In vivo efficacy of compound I on human breast cancer BT-474 xenograft model. When administered for 20 days, compared with the solvent control group, when compound I was at the dose of 0.05 mg/kg, 0.1 mg/kg and 0.3 mg/kg, the T/C were 44%, 23% and 16%, respectively, the TGI were respectively 77%, 109% and 118%. It could be known from the results that in the human breast cancer BT-474 xenograft tumor model, compound I had significant anti-tumor effects at doses of 0.05, 0.1 and 0.3 mg/kg, and had dose-dependent trend. The control drug PF05212384 in the 20 mg/kg group (T/C=15%, TGI=134%, p=0.006) had a significant antitumor effect compared with the solvent control group. Everolimus, 5 mg/kg (T/C=19%, TGI=113%, p<0.001), had a significant antitumor effect compared with the solvent control group. Compound I at the dose of 0.3 mg/kg had the similar anti-tumor effect as Everolimus at 5 mg/kg.

TABLE 11

Evaluation of antitumor efficacy of compound I on BT-474 xenograft tumor model (Based on data at day 20 after administration)

| Group | Tumor volume ($mm^3$)[a] (Day 20) | T/C[b](%) | TGI[b](%) |
|---|---|---|---|
| Solvent 1 | 338 ± 53 | — | — |
| PF05212384 (20 mg/kg) | 49 ± 6 | 15 | 134 |
| Solvent 2 | 430 ± 45 | — | — |
| Everolimus (5 mg/kg) | 82 ± 17 | 19 | 113 |
| Compound I (0.05 mg/kg) | 194 ± 49 | 44 | 77 |
| Compound I (0.1 mg/kg) | 94 ± 12 | 23 | 109 |
| Compound I (0.3 mg/kg) | 68 ± 8 | 16 | 118 |

Note:
[a]Mean ± SEM.
[b]Tumor growth inhibition was calculated from T/C and TGI (TGI (%) = $[1 - (T_{20} - T_0)/(V_{20} - V_0)] \times 100$).

Conclusion: Compound I significantly inhibited the growth of PIK3CA-mutated breast cancer tumor. In the very low dose group, 0.1 mg/kg and 0.3 mg/kg could cause tumor shrinkage, which had the similar efficacy with that of the control compound Everolimus (5 mg/kg, high dose).

Example 7 Efficacy Data of Compound I on Cervical Cancer Patient Carrying PIK3CA Mutation in Clinical Trials Clinical data: subject 1, female, 50 years old, underwent “extensive total hysterectomy+pelvic lymphadenectomy” on May 5, 2019; the postoperative pathology report showed cervical squamous cell carcinoma; postoperative adjuvant therapy was performed from May to August in 2019, and recurrence was found on imaging on Aug. 25, 2020; in first-line treatment, disease progression was found on imaging on Nov. 10, 2020; in second-line treatment, disease progression was found on imaging on Jan. 4, 2021; in third-line treatment, after disease progression in June, 2021, an informed consent was made on Jun. 18, 2021. Genetic detection was performed through ACCB human PIK3CA gene mutation detection kit. Genetic detection showed that the tumor carried PIK3CA mutation. She joined the "Clinical study of compound Ion the treatment of gynecological tumors with PIK3CA mutation": during the second tumor assessment period from Jul. 1, 2021 to Oct. 21, 2021, the tablets containing compound I were single administered with the dose of 1.1 mg once a day. The 1.1 mg dose comprised two tablets containing 0.5 mg of compound I and one tablet containing 0.1 mg of compound I. The baseline target lesion was lymph (left supraclavicular) 26 mm, right lower lobe 17 mm, left lower lobe 14 mm, lymph (retroperitoneum) 21 mm, a total diameter of 78 mm; the first tumor assessment was performed on Aug. 25, 2021, and the target lesion was lymph (left supraclavicular) 13 mm, right lower lobe 13 mm, left lower lobe 8 mm, lymph (retroperitoneum) 13 mm, a total diameter of 47 mm; compared with baseline, tumor shrinkage was 39.7%, and the efficacy evaluation was PR (partial response, the sum of the largest diameters of the target lesions was reduced by ≥30%, and it was maintained for at least 4 weeks); the second tumor assessment was performed on Oct. 21, 2021, and the target lesion was lymph 14 mm (left supraclavicular), right lower lobe 14 mm, and left lower lobe NE (existing, unmeasurable, less than 5 mm), lymph (retroperitoneum) 12 mm, a total diameter of less than 45 mm; compared with baseline, tumor shrinkage was greater than 42.3%, and the efficacy evaluation is PR (partial response, the sum of the maximum diameter of target lesions was reduced by ≥30%, and it was maintained for at least 4 weeks).

Conclusion: Compound I showed curative effect on PIK3CA-mutated cervical cancer in clinical trials. Third-line treatments such as radiotherapy and chemotherapy, chemotherapy plus angiogenesis inhibitors were ineffective for subject 1, and there was no treatment option. After administration of compound I, the curative effect was significant, and the tumor shrunk to PR (partial response, the sum of the maximum diameters of target lesions was reduced by ≥30%, and it was maintained for at least 4 weeks).

Example 8 Efficacy Data of Compound I on Ovarian Cancer Patient Carrying PIK3CA Mutation in Clinical Trials Clinical data: subject 2, female, 44 years old, underwent "cytoreductive surgery for ovarian cancer (full uterus+double appendages+omentum+appendectomy+right pelvic lymph node biopsy) on Apr. 27, 2020. Postoperative pathology showed clear cell carcinoma of the left ovary; first-line treatment was performed, and the last chemotherapy time was Oct. 11, 2020; CT on Oct. 27, 2020 showed the possibility of liver metastasis; "liver tumor resection+resection of abdominal cavity lesion+partial resection of diaphragm+diaphragm repair+lysis of intestinal adhesions" were performed on Nov. 23, 2020; postoperative pathology report showed clear cell carcinoma metastasis in the liver; second-line treatment in January 2021 was performed, and MRI showed the tumor progression on Apr. 8, 2021. Informed consent was obtained on Apr. 23, 2021. The previous gene detection report based on next-generation sequencing showed that the tumor carried PIK3CA mutation, and subject 2 participated in the "Clinical study of compound I on the treatment of gynecological tumors with PIK3CA mutation": during the second tumor assessment period from May 11, 2021 to Aug. 31, 2021, the tablets containing compound I were single administered with the dose of 1.1 mg once a day. The 1.1 mg dose comprised two tablets containing 0.5 mg of compound I and one tablet containing 0.1 mg of compound I; the baseline target lesion was the paracolic groove on the right side of the peritoneum (the longest diameter was 35 mm), the longest diameter of the peritoneal lesser omentum cavity was 47 mm, and the total diameter was 82 mm; the first tumor assessment on Jul. 6, 2021 showed the target lesion was (1) the paracolic groove on the right side of the peritoneum (not measurable, calculated based on a diameter of 5 mm), the longest diameter of the peritoneal lesser omentum cavity was 34 mm; the total diameter was 39 mm; the tumor shrinkage was 52.4% compared with the baseline; the efficacy evaluation was PR (partial response, the sum of the maximum diameters of target lesions was reduced by ≥30%, and it was maintained for at least 4 weeks); 2021 Aug. 30: second tumor evaluation, the target lesion was (1) the right paracolic groove of the peritoneum (not measurable, calculated based on a diameter of 5 mm), (2) the longest diameter of the peritoneal lesser omentum cavity was 28 mm; the total diameter was 33 mm; compared with the baseline, the tumor shrinkage was 59.8%; the efficacy evaluation was PR (partial response, the sum of the maximum diameters of target lesions was reduced by ≥30%, it was maintained for at least 4 weeks).

Conclusion: Compound I showed curative effect on PIK3CA-mutated ovarian cancer in clinical trials. Subject 2 was drug-resistant after second-line standard treatment, and there was no treatment option. After administration of compound I, the curative effect was significant, and the tumor shrunk to PR (partial response, the sum of the maximum diameters of target lesions was reduced by ≥30%, and it was maintained for at least 4 weeks) and continued to shrink (tumor shrinkage by 59.8%).

What is claimed is:

1. A method for treating PIK3CA-mutated cancer, comprising administering to a patient a therapeutically effective amount of compound I or a pharmaceutically acceptable salt thereof, wherein the structure of the compound I is as follows:

I

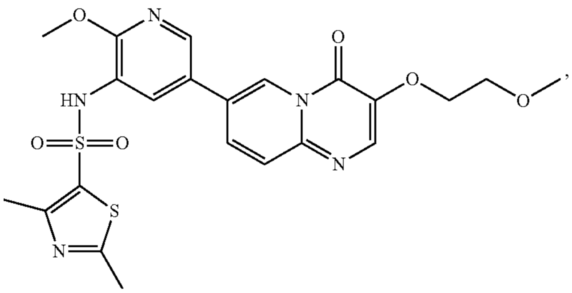

wherein the PIK3CA-mutated cancer is PIK3CA-mutated endometrial cancer, PIK3CA-mutated cervical cancer, or PIK3CA-mutated ovarian clear cell carcinoma.

2. The method for treating PIK3CA-mutated cancer according to claim 1, wherein the PIK3CA-mutated cancer is PIK3CA-mutated ovarian clear cell carcinoma.

3. The method for treating PIK3CA-mutated cancer according to claim 1, wherein the PIK3CA-mutated cancer is PIK3CA-mutated endometrial cancer.

4. The method for treating PIK3CA-mutated cancer according to claim 1, wherein the PIK3CA-mutated cancer is PIK3CA-mutated cervical cancer.

5. The method for treating PIK3CA-mutated cancer according to claim 1, wherein, the method further includes a step of detecting whether the patient carries PIK3CA gene mutation.

6. The method for treating PIK3CA-mutated cancer according to claim 1, wherein the administration dosage of the compound I or the pharmaceutically acceptable salt thereof is 0.1 mg per dose, 0.2 mg per dose, 0.3 mg per dose, 0.4 mg per dose, 0.5 mg per dose, 0.6 mg per dose, 0.7 mg per dose, 0.8 mg per dose, 0.9 mg per dose, 1.0 mg per dose, 1.1 mg per dose, 1.2 mg per dose, 1.3 mg per dose, 1.4 mg per dose, 1.5 mg per dose, 1.6 mg per dose, 1.7 mg per dose, 1.8 mg per dose, 1.9 mg per dose or 2.0 mg per dose.

7. The method for treating PIK3CA-mutated cancer according to claim 1, wherein the PIK3CA-mutated ovarian clear cell carcinoma is PIK3CA-mutated ovarian clear cell carcinoma with metastasis.

8. The method for treating PIK3CA-mutated cancer according to claim 1, wherein the PIK3CA-mutated ovarian clear cell carcinoma is ovarian clear cell carcinoma that is ineffective to first-line or second-line treatment.

9. The method for treating PIK3CA-mutated cancer according to claim 1, wherein the PIK3CA-mutated cervical cancer is PIK3CA-mutated cervical squamous cell carcinoma.

10. The method for treating PIK3CA-mutated cancer according to claim 1, wherein the PIK3CA-mutated cervical cancer is PIK3CA-mutated cervical cancer with metastasis.

11. The method for treating PIK3CA-mutated cancer according to claim 1, wherein the PIK3CA-mutated cervical cancer is cervical cancer that is ineffective to first-line treatment, second-line treatment or third-line treatment.

12. The method for treating PIK3CA-mutated cancer according to claim 1, wherein the compound I or the pharmaceutically acceptable salt thereof is presented in an oral dosage form.

13. The method for treating PIK3CA-mutated cancer according to claim 1, wherein the compound I or the pharmaceutically acceptable salt thereof is presented in a tablet form.

14. The method for treating PIK3CA-mutated cancer according to claim 1, wherein the administration dosage of the compound I or the pharmaceutically acceptable salt thereof is 0.1-2.0 mg per dose.

15. The method for treating PIK3CA-mutated cancer according to claim 1, wherein the administration frequency of the compound I or the pharmaceutically acceptable salt thereof is once a day or twice a day.

* * * * *